United States Patent [19]

Morgan et al.

[11] Patent Number: 5,196,330
[45] Date of Patent: Mar. 23, 1993

[54] TYPE II RESTRICTION ENDONUCLEASE, PME I, OBTAINABLE FROM PSEUDOMONAS MENDOCINA AND A PROCESS FOR PRODUCING THE SAME

[75] Inventors: Richard Morgan, Middleton; Bing Zhou, Beverly, all of Mass.

[73] Assignee: New England Biolabs, Inc., Beverly, Mass.

[21] Appl. No.: 710,040

[22] Filed: Jun. 3, 1991

[51] Int. Cl.$^5$ .................................................. C12N 9/22
[52] U.S. Cl. .................................... 435/199; 435/874
[58] Field of Search ............................... 435/199, 193

[56] References Cited

FOREIGN PATENT DOCUMENTS 193413  9/1986  European Pat. Off. .

OTHER PUBLICATIONS

Endow, et al. J. Mol. Biol. 112:521 (1977).
Waalwijk, et al. Nucleic Acids Res. 5:3231 (1978).
Gingeras, et al., Proc. Natl. Acad. Sci. U.S.A. 80:402 (1983).
Lunnen, et al. Gene 74:25–32 (1988).
Sanger, F. et al., Proc. Natl. Acad. Sci. U.S.A. 74:5463–5467 (1977).
Brown, N. L. et al., J. Mol. Biol. 140:143–148 (1980).

Primary Examiner—Charles L. Patterson, Jr.

[57] ABSTRACT

The present invention provides a novel type II restriction endonuclease obtainable from *Pseudomonas mendocina*. The endonuclease known as Pme I, recognizes the following nucleotide sequence and has a cleavage point indicated by the arrows:

5'-G T T T ↓ A A A C-3'
3'-C A A A ↑ T T T G-5'

Also described is a process for obtaining Pme I from *Pseudomonas mendocina*.

5 Claims, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 13 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

GGCCNNNNNG GCC    13

TYPE II RESTRICTION ENDONUCLEASE, PME I, OBTAINABLE FROM PSEUDOMONAS MENDOCINA AND A PROCESS FOR PRODUCING THE SAME

BACKGROUND OF THE INVENTION

The present invention relates to a new Type II restriction endonuclease, Pme I, obtainable from *Pseudomonas mendocina*, and to the process for producing the same.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. The majority of restriction endonucleases recognize sequences of 4 to 6 nucleotides in length, although recently a small number of restriction endonucleases which recognize 7 or 8 uniquely specified nucleotides have been isolated. Most recognition sequences contain a dyad axis of symmetry and in most cases all the nucleotides are uniquely specified. However, some restriction endonucleases have degenerate or relaxed specificities in that they recognize multiple bases at one or more positions in their recognition sequence, and some restriction endonucleases recognize asymmetric sequences. Hae III, which recognizes the sequence 5' GGCC 3', is an example of a restriction endonuclease having a symmetrical, non-degenerate recognition sequence, while Hae II, which recognizes 5' (Pu)GCGC(Py) 3' typifies restriction endonucleases having a degenerate or relaxed recognition sequence. Endonucleases with symmetrical recognition sequences generally cleave symmetrically within or adjacent to the recognition site, while those that recognize assymmetric sequences tend to cleave at a distance of from 1 to 18 nucleotides away from the recognition site. Over one hundred twenty-five unique restriction endonucleases have been identified among several thousands of bacterial species that have been examined to date.

Bacteria usually possess only a small number of restriction endonucleases per species. The endonucleases are named according to the bacteria from which they are derived. Thus, the species *Haemophilus aegyptius*, for example synthesizes 3 different restriction endonucleases, named HaeI, HaeII and HaeIII. These enzymes recognize and cleave the sequences (AT)GGCC(AT), (Pu)GCGC(Py) and GGCC respectively. *Escherichia coli* RY13, on the other hand, synthesizes only one enzyme, EcoRI, which recognizes the sequence GAATTC.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecule and cleaving them in each place that the recognition sequence occurs. The disintegration that results inactivates many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

More than 1000 restriction endonucleases have been isolated from bacterial strains. Of these, more than 125 recognize unique sequences, while the rest share common recognition specificities. Restriction endonucleases which recognize the same nucleotide sequence are termed "isoschizomers." Although the recognition sequences of isoschizomers are the same, they may vary with respect to site of cleavage (e.g., XmaI v. SmaI, Endow, et al., *J. Mol. Biol.* 112:521 (1977); Waalwijk, et al., *Nucleic Acids Res.* 5:3231 (1978)) and in cleavage rate at various sites (XhoI v. PaeR7I, Gingeras, et al., *Proc. Natl. Acad. Sci.* U.S.A. 80:402 (1983)).

There is a continuing need for novel type II restriction endonucleases. Although type II restriction endonucleases which recognize a number of specific nucleotide sequences are currently available, new restriction endonucleases which recognize novel sequences provide greater opportunities and ability for genetic manipulation. In particular, there are few endonucleases available which recognize eight specific nucleotides. These include Not I (GCGGCCGC), Sfi I (GGCCNNNNNGGCC) (SEQ ID NO: 1), Pac I (TTAATTAA), Sse8387 I (CCTGCAGG), Asc I (GGCGCGCC) and Fse I (GGCCGGCC), although Fse I is not commercially available. Type II restriction endonucleases which recognize eight nucleotides are particularly useful in the manipulation of very large DNA molecules, such as whole chromosomes, because the requirement of eight specified nucleotides for cleavage means that these enzymes cleave less frequently and produce a fewer, more managable number of fragments from a given DNA molecule. Each new unique endonuclease enables scientists to precisely cleave DNA at new positions within the DNA molecule, with all the opportunities this offers.

SUMMARY OF THE INVENTION

In accordance with the present invention, there is provided a novel restriction endonuclease obtainable from *Pseudomonas mendocina* NEB#698, hereinafter referred to as "PmeI", which endonuclease:

(1) recognizes the nucleotide sequence GTTTAAAC in a double-stranded DNA molecule as shown below,

5'-GTTT ↓ AAAC-3'
3'-CAAA ↑ TTTG-5'

(wherein G represents guanine, C represents cytosine, A represents adenine and T represents thymine);

(2) cleaves said sequence in the phosphodiester bonds between the T and A as indicated with the arrows; and (3) cleaves double-stranded lambda c1857 DNA at positions 8462 and 16296, cleaves Adeno2 DNA at position 13248, cleaves phage T7 DNA at positions 276 and 10723, and does not cleave pUC19, pBR322, phiX174, SV40, M13mp18 DNAs.

The present invention further relates to a process for the production of the novel restriction endonuclease Pme I, which process comprises culturing Pseudomonas mendocina under conditions suitable for expressing Pme I, collecting the cultured cells, obtaining a cell-free extract therefrom and separating and collecting the restriction endonuclease Pme I from the cell-free extract.

DETAILED DESCRIPTION OF THE INVENTION

Figure 1:
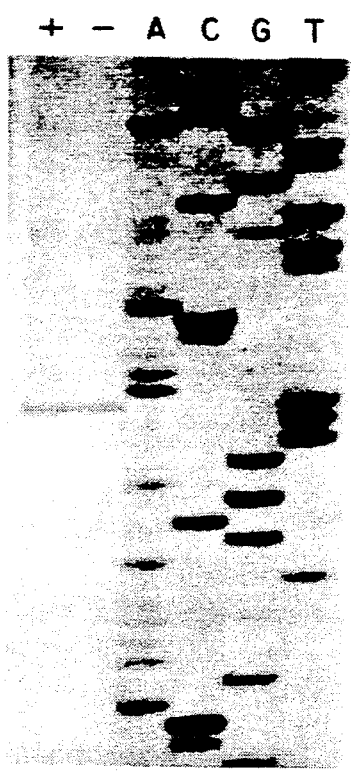
FIG. 1—A DNA sequencing gel used to determine the Pme I cleavage site. Legend: + indicates treatment with DNA polymerase (Klenow fragment) subsequent to Pme I cleavage of the primer extension product; — indicates no treatment with DNA polymerase subsequent to Pme I cleavage of the primer extension product; A, C, G, T lanes are standard dideoxy sequencing reaction products.

In accordance with the current invention, Pme I is obtained by culturing Pseudomonas mendocina strain NEB#698 and recovering the endonuclease from the cells. A sample of Pseudomonas mendocina NEB#698 has been deposited at the American Type Culture Collection (ATCC) on May 8, 1991 and bears the accession number 55181.

For recovering the enzyme of the present invention P. mendocina may be grown using any suitable technique. For example, P. mendocina may be grown in a media comprised of 10 g/L tryptone, 5 g/L yeast extract, 10 g/L NaCl, 1 g/L dextrose, 1 g/L MgCl$_2$.6H$_2$O (pH 7.2), which is incubated at 37° C. with agitation and aeration. Cells in the late logarithmic stage of growth are collected by centrifugation and either disrupted immediately or stored frozen at −70° C.

The Pme I enzyme can be isolated from P. mendocina cells by conventional protein purification techniques. For example, cell paste is suspended in a buffer solution and treated by sonication, high pressure dispersion or enzymatic digestion to allow extraction of the endonuclease by the buffer solution. Intact cells and cellular debris are then removed by centrifugation to produce a cell-free extract containing Pme I. The Pme I endonuclease is then purified from the cell-free extract by ion-exchange chromatography, affinity chromatography, molecular sieve chromotography, or a combination of these methods to produce the endonuclease of the present invention.

The endonuclease of the present invention along with its corresponding methylase may also be obtained using recombinant DNA techniques, such as the methylation selection technique disclosed by Wilson, al., EPO Publication No. 019413, the disclosure of which is herein incorporated by reference. As an example, DNA from a bacterial strain which contains an R-M system, such as P. mendocina, is purified, partially digested with cloning endonucleases, and ligated to an appropriate cleaved, dephosphorylated cloning vector. The ligated DNA is transformed into an appropriate host, such as E. coli, the transformants are pooled and the population of cloning vectors are purified to form libraries. The library of clones is then challenged by digesting with an endonuclease which will selectively destroy vectors which do not contain and express the methylase of the R-M system being cloned. Vectors which contain and express the methylase gene of interest will be modified at the endonuclease recognition sites of the challenging endonuclease and thus immune from cleavage. The challenged clone pools are then transformed back into the appropriate host to recover the undigested clones. The transformants may be screened for endonuclease activity or cycled through further rounds of purification and selection. Finally, individual transformants are selected and their DNA purified. These clones are analyzed for resistance to cleavage by the endonuclease of interest and for common insert DNA. Cell extracts prepared from transformants which demonstrate endonuclease resistance are assayed in vitro for methyltransferase and endonuclease activities.

A number of R-M systems have proved recalcitrant to cloning by the standard methylase selection method. These systems require modifications to the above approach. See Lunnen, et al., Gene 74:25–32 (1988), the disclosure of which is hereby incorporated by reference herein. For example, the endonuclease(s) used to form libraries may cleave in either or both of the R-M genes. In some systems the methylase and endonuclease genes may not be linked. In other systems, such as BamHI and DdeI, the methylase may not sufficiently protect against cleavage by the corresponding endonuclease, either because of inefficient expression of the methylase in the transformation host, because of the inherent control mechanism for expression of the methylase, or for unknown reasons. Another potential difficulty is that certain methylation patterns may be restricted in some hosts by endogenous host restriction systems, such as McrA, McrB or mrr, resulting in destruction of methylase clones. Another potential problem arises if the endonuclease sought to be cloned is not available in sufficient quantity or purity for methylase selection. Finally, in many systems difficulties are encountered in expressing the endonuclease gene in a host from a different bacterial genus.

The recognition sequence of the endonuclease of the present invention may be determined by mapping the locations of Pme I cleavage in various DNAs and comparing the DNA sequences of these regions for homology. The endonuclease Pme I was found to cleave lambda phage c1857 DNA in two places. These cut sites were mapped to approximate positions of 8500 and 16300 by simultaneously digesting lambda c1857 DNA with Pme I and with endonucleases which cleave at known positions, such as Apa I, SnaB I, Xba I, Xho I, Nhe I, Hind III, BstE II, Eco0109 I, Eag I and Kpn I. Pme I was also found to cleave Adeno2 DNA in one position, which was similarly mapped to approximately 13,500. The sequence GTTTAAAC was found to occur in lambda at 8459 and 16293 and in Adeno2 at 13245, and to occur only in these positions in these DNAs. The phage T7 site at 10720 was observed by Pme I cleavage and similar mapping techniques. The T7 site at 273 was not seen in digests with crude or semi-purified enzyme because of the small size of the fragment produced by cleavage at this site; however cleavage at this site is observed with purified Pme I. The sequence GTTTAAAC does not occur in pUC19, pBR322, PhiX174, M13mp18, and SV40 DNAs and these DNAs are not cleaved by Pme I. From this evidence we conclude that Pme I recognizes the sequence GTTTAAAC.

The point of cleavage within the Pme I recognition sequence may be determined through dideoxy sequencing analysis of the terminal base sequence obtained from Pme I cleavage of a suitable DNA substrate (Sanger, F. et al., (1977) PNAS 74:5463–5467, Brown, N. L., et al., (1980) *J. Mol. Biol.* 140, 143–148.). By the above referenced method (exemplified in example II) is was found that Pme I cleaves the phosphodiester bond between the most 3' T and the most 5' A in the recognition sequence GTTT/AAAC to produce a flush end, as indicated by the arrows:

The enzyme of the present invention also has the following properties:

(a) Optimal buffer composition: The optimal buffer tested was NEBuffer IV (20 mM Tris-acetate, 10 mM magnesium acetate, 50 mM potassium acetate, 1 mM DTT (pH 7.9)), supplemented with 100 ug/ml bovine serum albumin. Relative activity in NEBuffer I (10 mM Bis Tris Propane-HCl, 10 mM MgCl2, 1 mM DTT (pH 7.0)) and NEBuffer III (50 mM Tris-HCl, 10 mM MgCl2, 100 mM NaCl, 1 mM DTT (pH 7.9))was less than 10%, while relative activity in NEBuffer II (10 mM Tris-HCl, 10 mM MgCl2, 50 mM NaCl, 1 mM DTT (pH 7.9)) was approximately 25%.

(b) Heat Inactivation: 20 units of Pme I in 100 ul NEBuffer IV can be inactivated in twenty minutes at 65° C.

(c) Enzyme Stability: 1 unit of Pme I is required to cleave 1 ug Lambda phage DNA in 50 uls NEBuffer IV to completion in sixteen hours at 37° C.

The following examples are given to illustrate embodiments of the present invention as it is presently preferred to practice. It will be understood that the examples are illustrative, and that the invention is not to be considered as restricted except as indicated in the appended claims.

EXAMPLE I

Production of PmeI Endonuclease

*Pseudomonas mendocina* strain NEB 698 (ATCC#55181) was grown in media consisting of 10 g/l tryptone, 5 g/l yeast extract, 10 g/l NaCl, 1 g/l magnesium chloride hexahydrate, 1 g/l glucose (adjusted to pH 7.2). The cells were incubated at 37° C. until late logarithmic stage with aeration and agitation. The cells were harvested by centrifugation and stored frozen at −70° C.

96 grams of the cells obtained above were suspended in three volumes buffer A (20 mM Tris-HCl, 0.1 mM EDTA, 6 mM 2-mercaptoethanol, 5% glycerol, pH 7.6 at 10° C.) adjusted to 50 mM NaCl. The cell suspension was sonicated until approximately 80 mg protein per gram of cells was released. The lysate was centrifuged at 15,000 rpm for 120 minutes at 4° C. in a Beckman JA17 rotor. 350 ml of supernatant was obtained containing approximately 800,000 units of Pme I and 6970 mg of soluble protein.

The supernatant solution was applied to a 350 ml DEAE-Sepharose column equilibrated in buffer A adjusted to 50 mM NaCl. The flow-through was batch collected. A 200 ml wash of buffer A adjusted to 50 mM NaCl was applied to the DEAE column and collected with the column flow-through. The DEAE flow-through/wash contained at least 800,000 units of Pme I activity and 1188 mg of soluble protein (an 83% purification from total protein).

The DEAE flow-through/wash containing the Pme I activity was applied to a 49 ml Heparin-Sepharose column equilibrated in buffer A adjusted to 50 mM NaCl. The column was washed with 250 mls buffer A adjusted to 50 mM NaCl. The protein solution was eluted with a 500 ml gradient of 50 mM to 1M NaCl in buffer A. Fractions were tested for Pme I and exonuclease activity, as described below. The Pme I activity eluted at approximately 45% of the gradient volume. 30 mls containing 480,000 units of Pme I activity in a total of 20 mg soluble protein were pooled and dialysed against buffer B (20 mM KPO4, 0.1 mM EDTA, 6 mM 2-mercaptoethanol, 5% glycerol, pH 6.7), adjusted to 50 mM NaCl. A peak of contaminating exonuclease activity eluted at approximately 37% of the gradient volume, although contaminating exonuclease was present in all the fractions tested. The Pme I pool from the heparin-sepharose column represents a 98% purification from total protein.

The dialysate was applied to a WCX 7 um HPLC column (Custom LC, Inc.) equilibrated in buffer B adjusted to 50 mM NaCl. The column was washed with buffer B adjusted to 50 mM NaCl and the Pme I enzyme was eluted with a 50 ml gradient of 50 mM to 0.6M NaCl in buffer B. The Pme I activity eluted at approximately 0.30M NaCl. A 4 ml pool of Pme I containing approximately 384,000 units of Pme I activity was collected. A contaminating endonuclease eluted at approximately 0.22M NaCl, and contaminating exonuclease activity eluted at 0.25M and 0.34M NaCl.

The Pme I eluent was applied to a 2.5 cm by 110 cm G-75 size exclusion column equilibrated in buffer C (20 mM Tris-HCl, 6 mM 2-mercaptoethanol, 0.1 mM EDTA, 10% glycerol, pH 7.5) adjusted to 0.5M NaCl. Buffer C adjusted to 0.5M NaCl was used to elute the protein solution from the G-75 column. Pme I activity eluted at approximately 250 mls. A 42 ml pool containing 90,000 units of Pme I was collected and dialyzed against buffer B adjusted to 50 mM NaCl. An exonuclease activity eluted after 280 mls.

The dialysate obtained above was applied to a Mono-S FPLC column (Pharmacia) equilibrated in buffer B adjusted to 50 mM NaCl. The protein solution was eluted with a 31 ml gradient of 50 mM to 0.6M NaCl. The Pme I activity eluted at approximately 0.16M NaCl, while a contaminating exonuclease eluted at approximately 0.20M NaCl.

The Pme I obtained was substantially pure and free of contaminating endonuclease and exonuclease activities. Bovine serum albumin was added as a stabilizer to a final concentration of 200 ug/ml and the Pme I was dialyzed against storage buffer (50% glycerol, 50 mM NaCl, 20 mM Tris-HCl, 0.1 mM dithiothreitol, pH 7.5). The final pool of Pme I contained 48,000 units of Pme I activity, which represents a 6% recovery.

Activity Determination

Pme I activity: Samples of from 1 to 10 uls were added to 25 uls of substrate solution consisting of 1× NEBuffer IV containing 0.5 ug Lambda phage DNA. The reaction was incubated at 37° C. for 5 to 60 mins. The reaction was terminated by adding 5 uls of a stop solution (50% glycerol, 50 mM EDTA pH 8.0, and 0.02% Bromophenol Blue). The reaction mixture was applied to a 0.7% agarose gel and electrophoresed. The bands obtained were identified in comparison with DNA size standards.

Exonuclease activity: A 5 ul sample of the protein solution was added to 50 ul of NEBuffer IV, containing 25 ug/ml $^3$H-DNA. The reaction was incubated for one hour and the number of soluble and insoluble counts compared.

Unit Definition: One unit of Pme I is defined as the amount of Pme I required to completely cleave 1.0 ug of Lambda DNA in a total reaction volume of 50 ul NEBuffer IV, supplemented with 100 ug/ml bovine serum albumin, within one hour at 37° C.

Optimal Buffer Conditions: For optimum Pme I activity NEBuffer IV (50 mM potassium acetate, 20 mM Tris-acetate, 10 mM magnesium acetate, 1 mM dithiothreitol (pH 7.9 at 25° C.)), supplemented with 100 ug/ml bovine serum albumin, was used.

EXAMPLE II

Determination of the Pme I Cleavage Site

The location of Pme I cleavage relative to the recognition sequence was determined by cleavage of a primer extension product, which was then electrophoresed alongside a set of standard dideoxy sequencing reactions produced from the same primer. The template, pRM517.122-3, was employed because it has a Pme I recognition site located 79 base pairs 3' of the pUC19 priming site for primer NEB#1201 (5' dAACAGCTATGACCATG 3').

Denaturing the Double-Stranded Template 3 ug of pRM517.122-3 miniprep prepared plasmid (the template) was dissolved in a total of 20 ul dH$_2$O in a 1.5 ml eppendorf tube. 2 ul of 2M NaOH, 2 mM EDTA was added and the solution incubated 5 minutes at room temperature, following which 7 ul dH$_2$O (4° C.), 7 ul 3M NaAcetate pH 6.0 (4° C.) and 75 ul Ethanol (4° C.) were added rapidly. The solution was immediately placed in a dry ice/2-propanol bath for 15 minutes to precipitate the DNA. The DNA was pelleted by centrifugation for 10 minutes in an eppendorf centrifuge, 95% of the supernatant was removed by aspiration, 300 ul of 70% ETOH/30% dH$_2$O was added and the solution centrifuged for 5 minutes, followed by removal of approximately 95% of the supernatant. The pellet was then completely dried in a speed-vac apparatus for 10 minutes.

Sequencing Reactions

To the dried pellet were added 13.5 ul dH$_2$O, 2.25 ul 10× sequencing buffer (75 mM Tris pH 7.6, 55 mM DTT, 50 mM MgCl$_2$), and 1.5 ul of primer (NEB#1201) solution of approximately 1.0 uM concentration. The solution was incubated at 37° C. for 30 minutes to anneal the primer. 3 ul of [α-35S] dATP at 800 Ci/mmole, 10 mCi/ml was added. 1.5 ul (7.5 units) Klenow fragment DNA polymerase (NEB #210) was added. This solution is called the TPK mixture. 3.2 ul of the TPK mixture was aliquoted into 3 ul of the deoxy/dideoxy nucleotide reaction mixtures (NEB#410) for the A,C,G and T sequencing reactions. The remaining TPK mixture was added to 9 ul of A sequencing reaction mix which contained no dideoxy nucleotides to create a labeled strand of DNA extending through the Pme I recognition site. The reactions were incubated 15 minutes at 37° C. 1 ul of dNTP chase solution (NEB #410) was added to the A,C,G and T reactions and 3 ul chase was added to the extension reaction. The reactions were incubated an additional 15 minutes at 37° C. 6 ul stop solution (NEB #410) was added to the A,C,G and T sequencing reactions and these were stored at −20° C. until run on a sequencing gel. The extension reaction was incubated at 70° C. for 25 minutes to inactivate the DNA polymerase (Klenow), then incubated at room temperature for 10 minutes. 9 ul of the extension reaction was placed in one 0.5 ml eppendorf tube and 6 ul were placed in a second tube. To the 9 ul tube was added 1 ul (approximately 1 unit) Pme I endonuclease. The reaction was mixed and 2 ul were transferred to the second tube. The enzyme digest reactions were incubated at 37° C. for 30 minutes. Following digestion 4 ul of the reactions were removed and mixed with 5 ul stop solution. To the remaining 4 ul was added 0.25 ul (1.25 units) Klenow fragment and the reaction incubated at room temperature for 15 minutes, after which 5 ul of stop solution was added. The enzyme digest reactions were also stored at −20° C. prior to electrophoresis. The reaction products were electrophoresed on an 8% Bis-Acrylamide sequencing gel, with the Pme I digestions of the extension reaction next to the set of sequencing reactions produced from the same primer.

Digestion of the extension reaction product with Pme I endonuclease produced a band which co-migrated with the fourth nucleotide of the Pme I recognition sequence GTTTAAAC. Treatment with Klenow fragment following Pme I digestion produced a fragment which also co-migrated with the fourth nucleotide in the Pme I recognition sequence GTTTAAAC. These results indicate Pme I cleaves DNA between the fourth and fifth bases in its recognition sequence 5' GTTT/AAAC 3' to produce a blunt, or flush end.

---

What is claimed is:

1. A substantially pure Type II restriction endonuclease obtainable from *Pseudomonas mendocina* (ATCC#55181) recognizing the following base sequence in double-stranded deoxyribonucleic acid molecules:

5'-G T T T ↓ A A A C-3'
3'-C A A A ↑ T T T G-5' and having a cleavage position defined by the arrows.

2. The type II restriction endonuclease of claim 1, cleaving double-stranded deoxyribonucleic acid lambda cI857 in two and adeno-2 in one position.

3. A method for obtaining the Type II restriction endonuclease of claim 1, comprising cultivating a sample of *Pseudomonas mendocina* under conditions favoring the production of said endonuclease and separating said endonuclease therefrom.

4. The type II restriction endonuclease of claim 1, wherein the restriction endonuclease is inactivated by incubation at 65° C. for 20 minutes.

5. The type II restriction endonuclease of claim 1, wherein the restriction endonuclease is purified from *Pseudomonas mendocina*(ATCC#55181).

* * * * *